US011883212B2

(12) United States Patent
Young et al.

(10) Patent No.: US 11,883,212 B2
(45) Date of Patent: Jan. 30, 2024

(54) SURGICAL INSTRUMENT TABLE AND DRAPE THEREFOR

(71) Applicant: VARIAMED LLC, Chattanooga, TN (US)

(72) Inventors: Christopher B. Young, Chattanooga, TN (US); David Tate, Chattanooga, TN (US)

(73) Assignee: VARIAMED LLC, Chattanooga, TN (US)

( * ) Notice: Subject to any disclaimer, the term of this patent is extended or adjusted under 35 U.S.C. 154(b) by 478 days.

(21) Appl. No.: 17/149,887

(22) Filed: Jan. 15, 2021

(65) Prior Publication Data

US 2022/0160452 A1 May 26, 2022

Related U.S. Application Data

(60) Provisional application No. 63/116,319, filed on Nov. 20, 2020.

(51) Int. Cl.
*A61B 50/15* (2016.01)
*A61B 46/10* (2016.01)

(52) U.S. Cl.
CPC .............. *A61B 50/15* (2016.02); *A61B 46/10* (2016.02)

(58) Field of Classification Search
CPC ... A61B 50/15; A61B 2050/155; A61B 46/10; A47B 2037/005
See application file for complete search history.

(56) References Cited

U.S. PATENT DOCUMENTS

| | | | | |
|---|---|---|---|---|
| 3,998,221 A * | 12/1976 | Collins | ................. | A61B 46/23 108/90 |
| 4,051,845 A * | 10/1977 | Collins | ................. | A61B 46/23 128/855 |
| 4,476,860 A * | 10/1984 | Collins | ................. | A61B 46/23 128/853 |
| 5,170,804 A * | 12/1992 | Glassman | .............. | A61B 50/10 128/849 |
| 5,333,326 A * | 8/1994 | Faries, Jr | .............. | A61F 7/0241 604/113 |
| 5,435,322 A * | 7/1995 | Marshall | ................ | A61B 46/10 128/849 |
| 5,522,095 A * | 6/1996 | Faries, Jr | ............... | A61B 46/10 4/639 |
| 5,871,015 A * | 2/1999 | Lofgren | ................. | A61B 50/13 128/849 |
| 6,019,102 A * | 2/2000 | Becker | ................... | A61B 50/15 128/849 |
| 6,189,459 B1 * | 2/2001 | DeAngelis | ............. | A61B 50/10 108/147.21 |
| 6,345,621 B1 * | 2/2002 | Chandler | ............... | A61B 46/00 128/853 |

(Continued)

*Primary Examiner* — Stanton L Krycinski
(74) *Attorney, Agent, or Firm* — Finch & Maloney PLLC

(57) ABSTRACT

A multi-tiered surgical table and a fitted drape for the table are disclosed. The table has a pair of table tops: a rearward, inclined top at a first elevation and a forward top at a lower second elevation. The drape has top panels corresponding in shape to the table tops, with a step panel therebetween to accommodate the change in elevation. The drape is provided, front, top and rear with receptacles for fluids and waste materials and pockets for surgical supplies such as sponges.

19 Claims, 7 Drawing Sheets

(56) References Cited

U.S. PATENT DOCUMENTS

| | | | | |
|---|---|---|---|---|
| 6,497,233 B1* | 12/2002 | DeAngelis | A61B 46/10 | 128/849 |
| 7,104,201 B2* | 9/2006 | Comeaux | A61B 46/10 | 108/90 |
| 8,459,265 B2* | 6/2013 | Young | A61B 50/15 | 128/853 |
| 8,689,704 B2* | 4/2014 | Hodges | A61B 46/10 | 312/319.9 |
| 8,707,961 B1* | 4/2014 | Kazravan | A61B 50/10 | 128/849 |
| 9,393,075 B2* | 7/2016 | Ghosh | A61B 46/10 | |
| 9,713,498 B2* | 7/2017 | Malackowski | A61B 90/361 | |
| 9,737,363 B2* | 8/2017 | Houde | A61B 50/13 | |
| 10,070,924 B2* | 9/2018 | Lother | A61B 50/15 | |
| 10,271,917 B2* | 4/2019 | Gerstner | A61B 50/15 | |
| 10,512,515 B2* | 12/2019 | Bailey | A61B 34/37 | |
| 10,925,683 B2* | 2/2021 | Gerstner | A61B 50/13 | |
| 11,020,199 B2* | 6/2021 | Chua | A61B 46/20 | |
| 11,246,675 B2* | 2/2022 | Menut | A61B 46/20 | |
| 11,284,959 B2* | 3/2022 | Bailey | A61B 34/74 | |
| 11,517,388 B2* | 12/2022 | Dine | A61B 46/00 | |
| 2003/0233964 A1* | 12/2003 | Comeaux | A61B 50/10 | 108/90 |
| 2004/0118410 A1* | 6/2004 | Griesbach, III | A61B 46/23 | 128/852 |
| 2004/0194673 A1* | 10/2004 | Comeaux | A61B 50/13 | 108/90 |
| 2006/0260515 A1* | 11/2006 | Hodges | A61B 50/13 | 108/6 |
| 2008/0149001 A1* | 6/2008 | Hodges | A61B 50/15 | 108/6 |
| 2010/0022981 A1* | 1/2010 | Goodman | A61F 13/551 | 604/385.13 |
| 2014/0041669 A1* | 2/2014 | Houde | A61B 50/15 | 128/849 |
| 2014/0138269 A1* | 5/2014 | Ghosh | A61B 90/30 | 206/370 |
| 2014/0216305 A1* | 8/2014 | Hodges | A61B 50/15 | 108/3 |
| 2014/0353189 A1* | 12/2014 | Lotosky-Compton | A61B 46/23 | 206/370 |
| 2016/0262842 A1* | 9/2016 | Sellers | A61B 46/10 | |
| 2022/0346901 A1* | 11/2022 | Haack | A61B 46/40 | |

* cited by examiner

SURGICAL INSTRUMENT TABLE AND DRAPE THEREFOR

TECHNICAL FIELD

The present invention relates to accessories for surgical instruments. More particularly, the present invention provides a two-tiered instrument table and a unitary drape for covering such a table.

BACKGROUND OF THE PRESENT INVENTION

Tiered surgical instrument tables provide medical personnel access to surgical equipment and supplies for use during a surgical procedure.

Tiered surgical tables can be difficult to drape properly. Often, several drapes sheets are placed in overlapping relation. Alternatively, at least one fitted surgical drape is available for draping a tiered surgical table so as to isolate the sterile lower tier surface from a contaminated underside surface of the upper tier. The fitted drape includes a bottom sheet that covers the lower tier and a top sheet that covers the upper tier. A middle sheet, which attaches to the top surface of the bottom sheet and to a front edge of the top sheet, spans the open gap between the two tiers. However, this drape has drawbacks to its use, as there are open gaps on the sides of the drape between the tiers and proper installation is not readily accomplished.

Accordingly, there is a need in the art for an improved drape to cover tiered surgical tables. It is to such that the present invention is directed.

BRIEF SUMMARY OF THE INVENTION

Wherefore, it is an object of the present invention to overcome the above mentioned shortcomings and drawbacks associated with the prior art.

An object of this invention is to provide a tiered table for a surgical environment, and a sterile fitted drape specifically designed for the table.

Another object of the invention is to simplify the draping procedure, and to make drape removal quick and easy.

Other objects, advantages, and features of the present invention will become readily apparent from the following detailed description in conjunction with the drawings and the appended claims.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. The invention will now be described, by way of example, with reference to the accompanying drawings in which.

Figure 1:
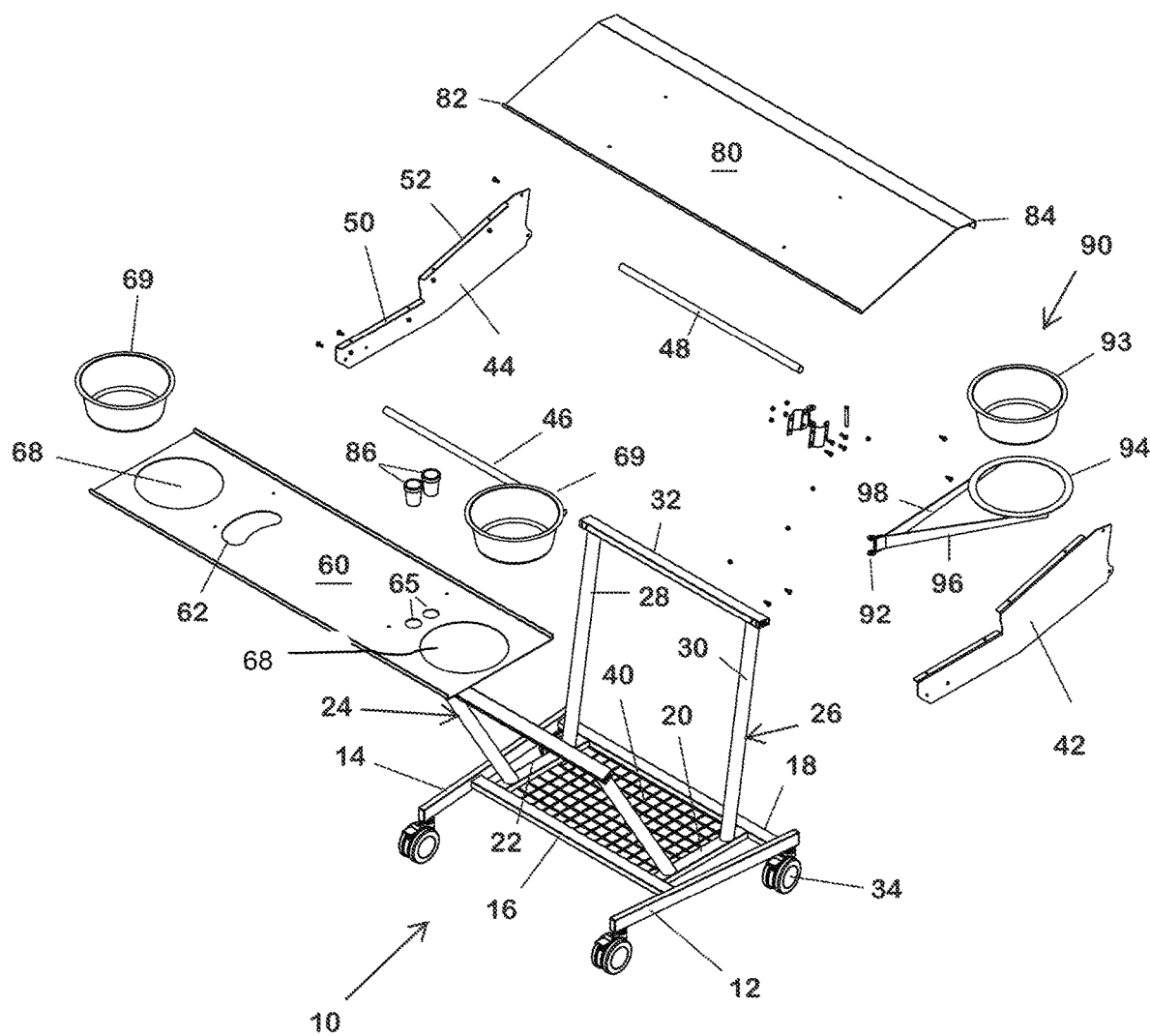
FIG. 1 is an exploded isometric view of a surgical table embodying a first aspect of the invention.
Figure 2:
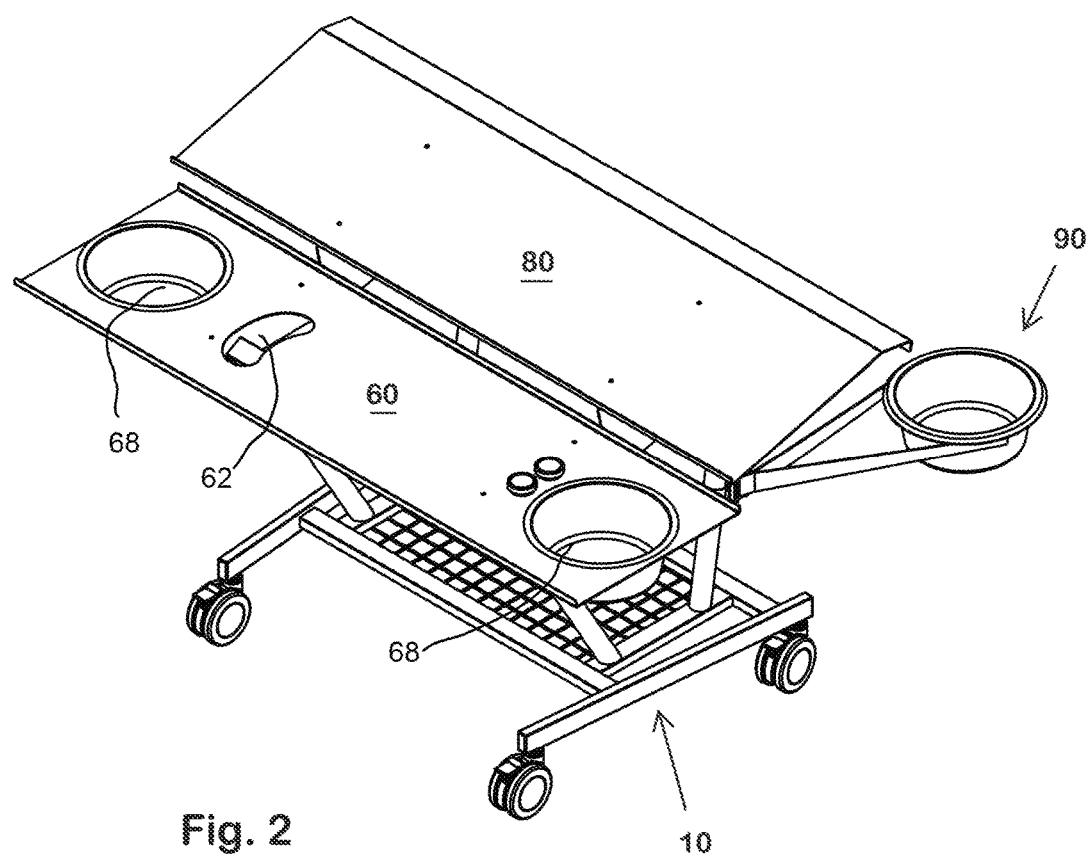
FIG. 2 is an unexploded isometric view thereof.
Figure 3:
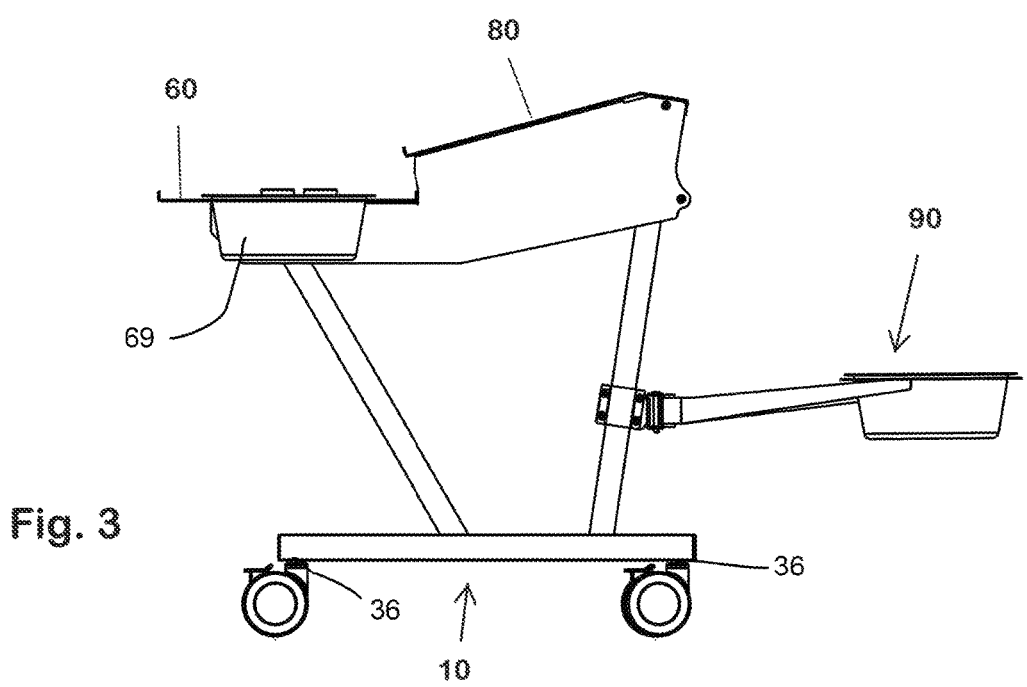
FIG. 3 is a right side elevation thereof.
Figure 4:
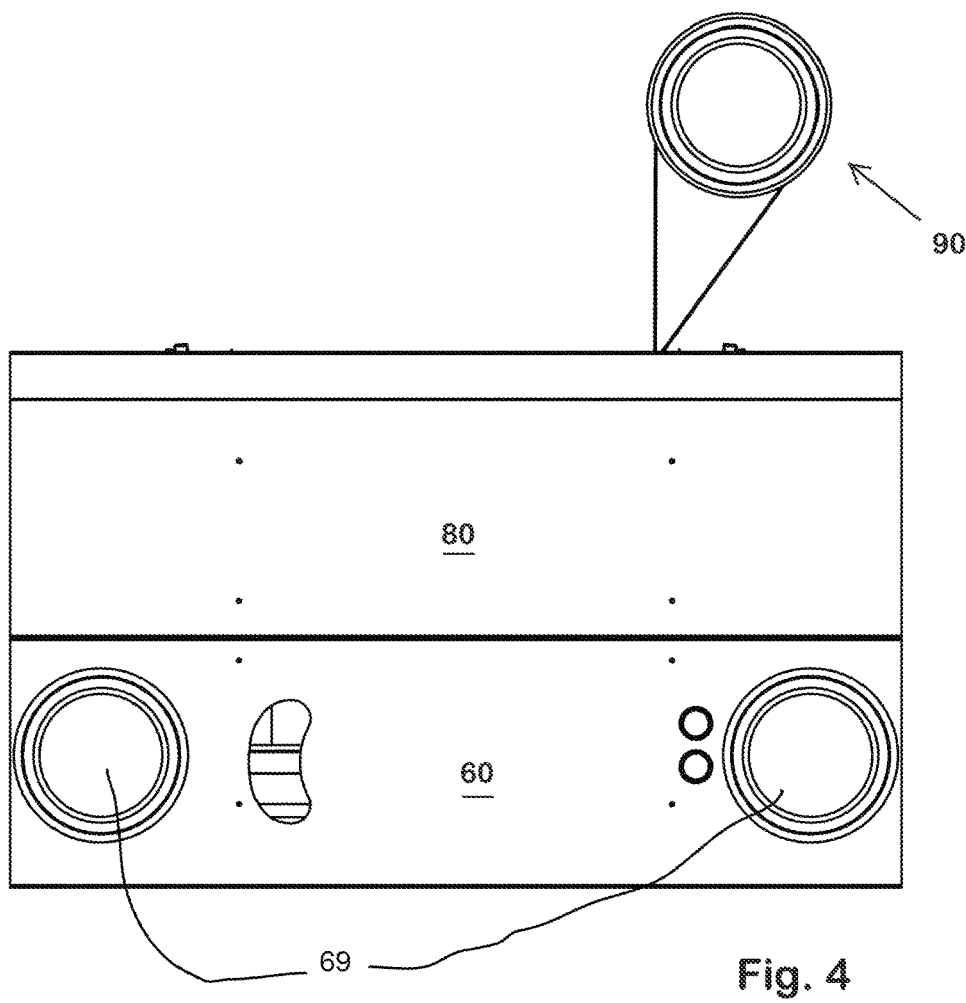
FIG. 4 is a top plan view thereof.
Figure 5:
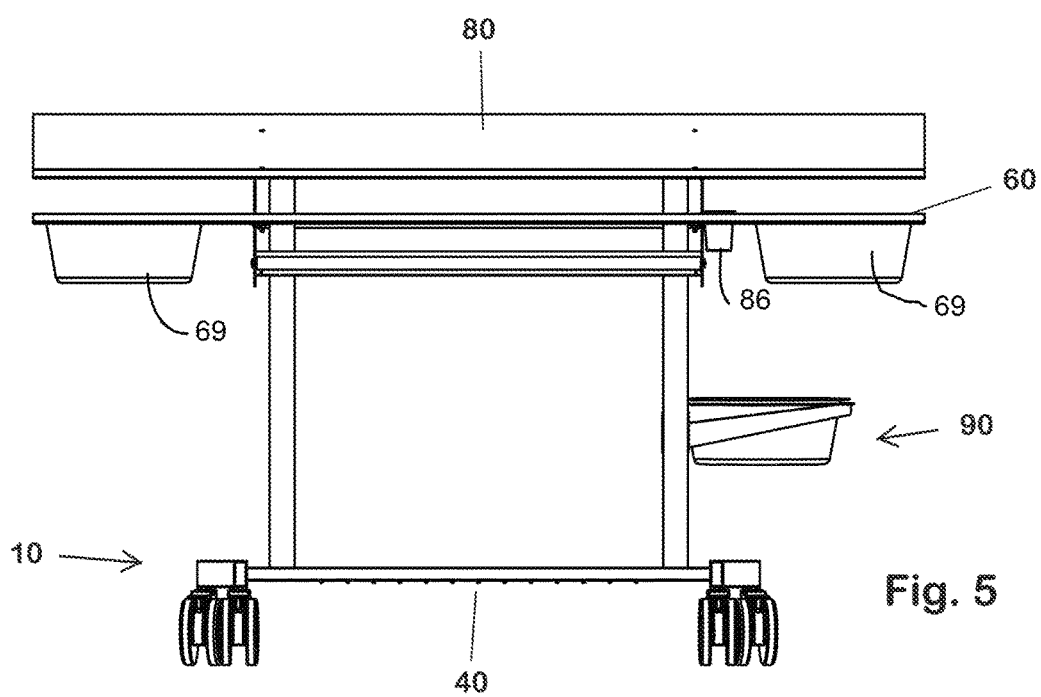
FIG. 5 is a front elevation thereof.

It should be understood that the drawings are not necessarily to scale and that the disclosed embodiments are sometimes illustrated diagrammatical and in partial views. In certain instances, details which are not necessary for an understanding of this disclosure or which render other details difficult to perceive may have been omitted. It should be understood, of course, that this disclosure is not limited to the particular embodiments illustrated herein.

DESCRIPTION OF THE PREFERRED EMBODIMENTS

The present invention will be understood by reference to the following detailed description, which should be read in conjunction with the appended drawings. It is to be appreciated that the following detailed description of various embodiments is by way of example only and is not meant to limit, in any way, the scope of the present invention.

With reference to FIGS. 1-5, a table embodying the invention has a welded chassis 10, which supports a pair of spaced table tops 60, 80.

The chassis 10 comprises a pair of horizontal side rails 12, 14, which diverge slightly toward the rear of the chassis. The side rails 12, 14 are interconnected by front and rear rails 16, 18. A pair of parallel horizontal members 20, 22 extend between the front and rear rails inboard of the side rails. The horizontal members 20, 22 support front and rear braces 24, 26, which diverge upwardly away from the horizontal members/struts 20, 22. Neither brace 24, 26 is vertical; the forward brace 24 leans toward the front of the chassis 10, and the rear brace 26 leans toward the rear. Each brace 24, 26 is formed from a pair of parallel tubes 28, 30, welded to either end of a horizontal bar 32.

Lockable casters 34, attached to either end of the left and right rails 12, 14, provide rolling support for chassis 10. Some or all of the casters 34 may have kingpins 36 (FIG. 3) to allow the casters 34 to pivot.

A tray 40, preferably in the form of a metal grill, is fitted in the rectangular area between the struts 20, 22 and the front and rear rails 16, 18. Alternatively, the grill could be made of expanded metal, or might be a molded plastic element, The table tops 60, 80 are supported by a pair of parallel spaced side panels 42, 44, made of sheet metal, which bear against the ends of the horizontal bars 32 and are affixed thereto by fasteners such as bolts. Horizontal handlebars 46, 48 (FIG. 1) reinforce the mounting of the side panels.

The top edges of the side panels have inwardly turned horizontal flanges 50, 52. The table tops 60, 80 rest on these flanges, to which they are connected by rivets or removable fasteners 54.

As shown each of the table tops 60, 80 is non-adjustably supported by the chassis 10, and the tops 60, 80 are situated at different heights so that one top 80 is higher and one top is lower 60. Additionally, the tops 60, 80 are non-parallel, with the front edge of the higher top 80 lying substantially above the rear edge of the lower top 60.

The front table top 60 has an aperture 62 for receiving a kidney basin, and a pair of holes 65 for receiving specimen cups 86. Such receptacles are preferably built into the drape described below. Two basin holes 68 are also provided, at opposite ends of the table top 60; these accept basins 69 intended to receive corresponding receptacles built into the drape.

The rear table top 80 has an upturned front edge flange 82, to keep instruments from rolling off, and a downturned rear edge flange 84.

At the rear of the frame, a pivotal bucket bracket assembly 90 is clamped to one of the front and the rear braces 24, 26. The bracket has a hinge 92, not shown in detail, so that a "kick bucket" 93 held by the bracket may be swung out the way when necessary. A hoop 94 for receiving the bucket is secured to the hinge by a pair of welded arms 96, 98.

Figure 11:
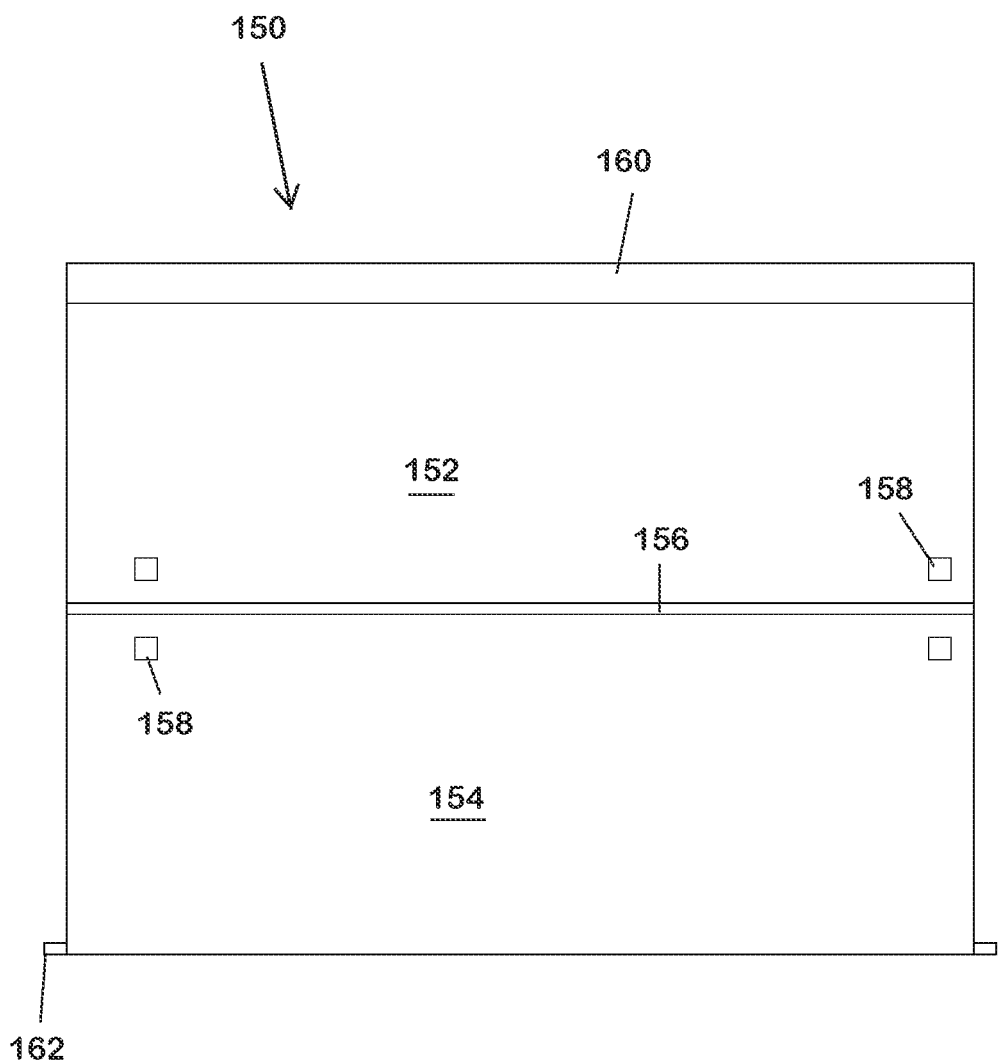
FIG. 11 is a layout view of a removable sterile barrier for protecting the drape surface, the barrier being shown in a folded configuration is FIGS. 6 and 7.

With reference to FIGS. 6-11, a drape pack for covering the table described above comprises two elements: a drape assembly 110 and a sterile barrier 150 (FIG. 11).

The drape assembly 110 (FIG. 6) comprises a fitted drape 112 having upper and lower top panels 114, 116 corresponding to the two table tops, with a short vertical step panel 118 between the two top panels 114, 116. The drape 112 also has a front panel 120, two side panels 122, and a rear panel 126 (see FIGS. 9 and 10), all of which hang a distance of about seventeen inches below the level of the front table, when the drape 112 is installed. The panels 116, 118, 120 and 126 have pockets 130, 132, 135 or other features built in, or permanently attached, as described below.

Figure 6:
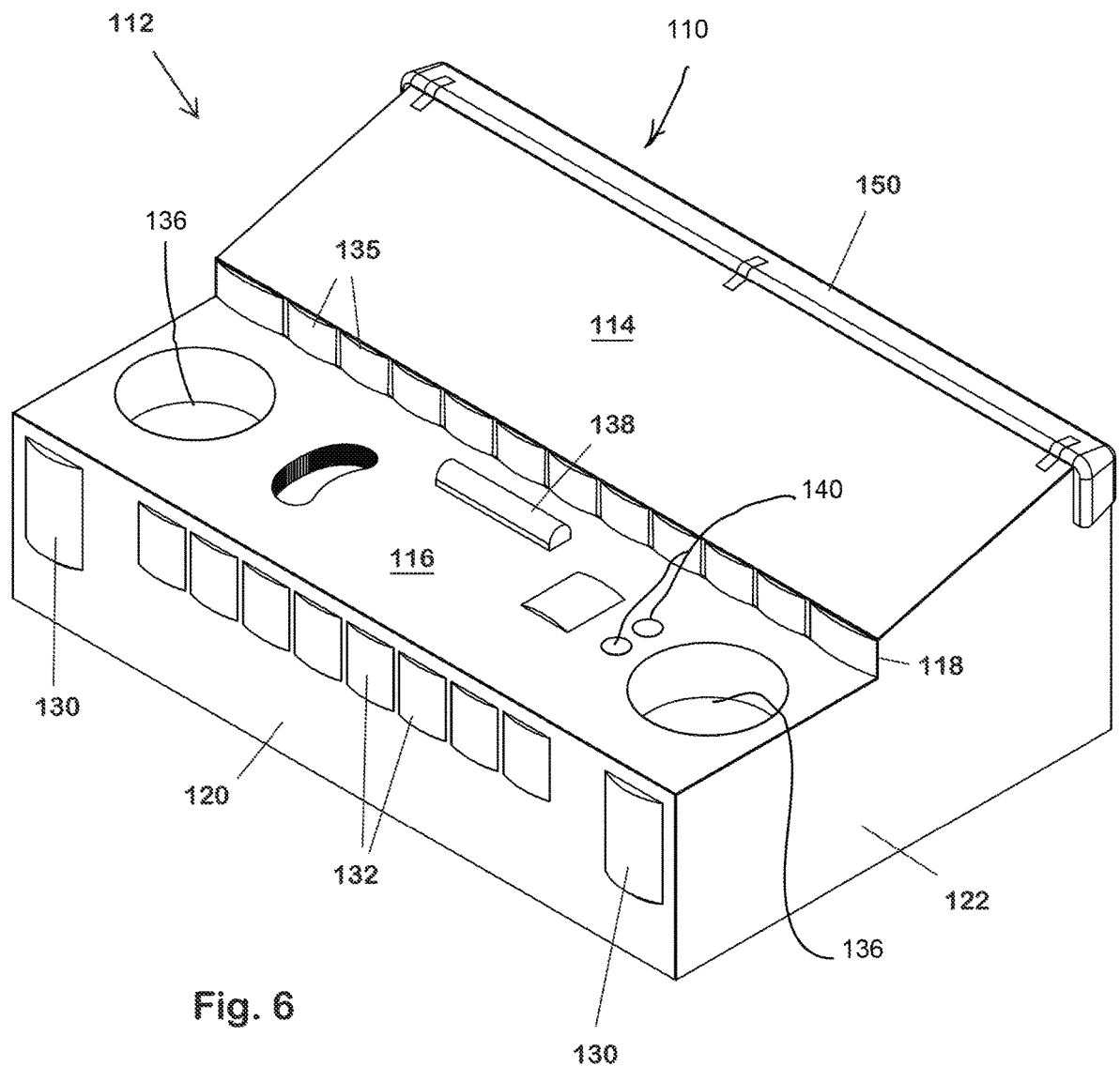
FIG. 6 is an isometric view of a drape embodying a second aspect of the invention, the drape being shown in the configuration it would have when installed over the table of FIG. 2.
Figure 8:
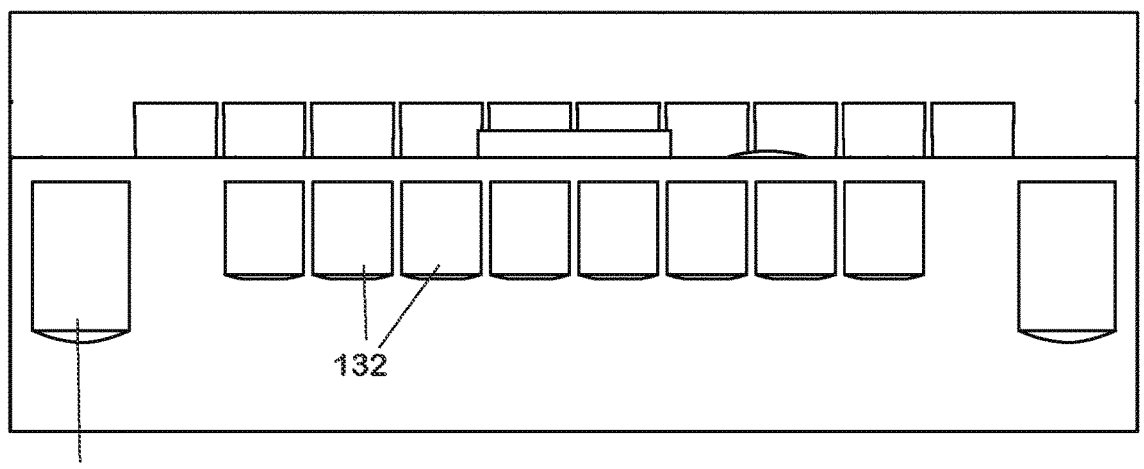
FIG. 8 is front elevation thereof.
Figure 9:
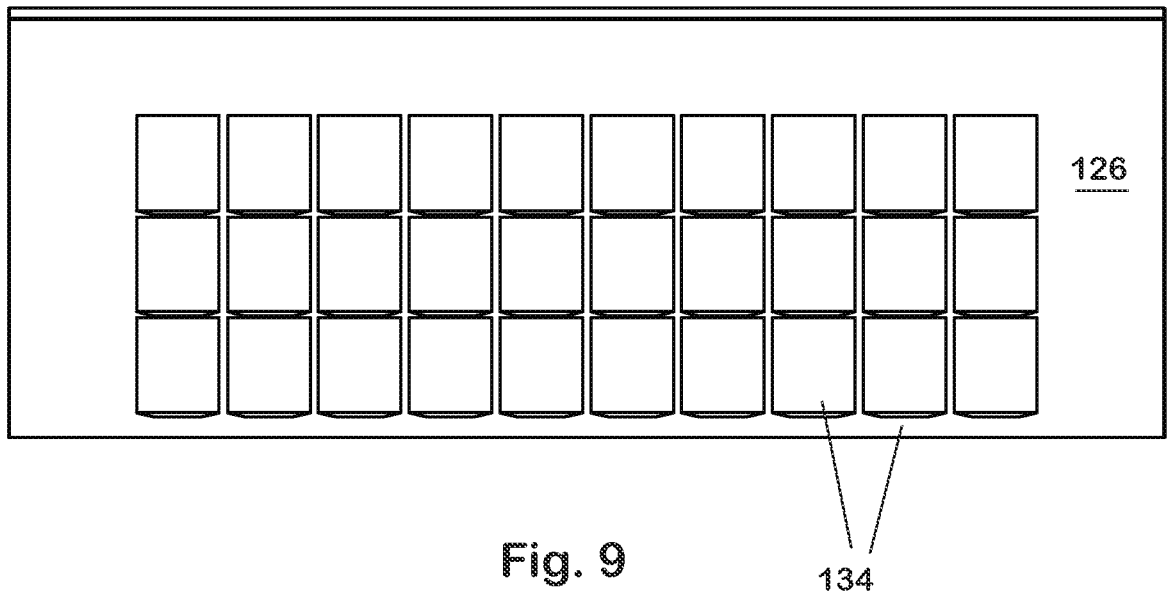
FIG. 9 is a rear elevation thereof.
Figure 10:
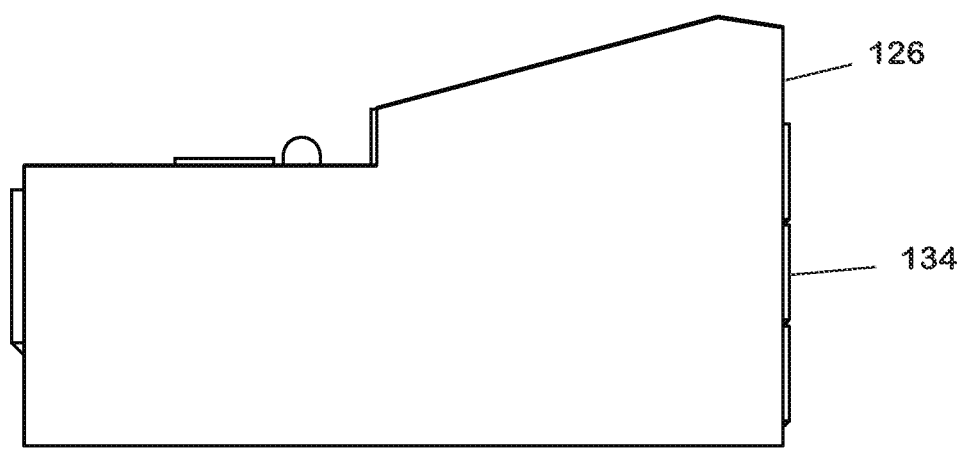
FIG. 10 is a right side elevation thereof.

As best seen in FIGS. 6 and 8, the front panel 120 of the drape has two refuse pockets 130, one at either end, and an array of (e.g., eight) smaller pockets 132 for lap sponges. These pockets are secured to the drape material during manufacture by welding or an adhesive.

The rear panel of the drape (FIG. 9) has and array of (e.g., thirty) pockets 134 for refuse.

The step panel 118 of the drape (FIGS. 6 and 8) has an array of (e.g., twelve) polyethylene storage pockets 135 disposed along the full width of the step.

As best seen in FIG. 6, the lower top panel of the drape has two polyethylene seven-quart basin recesses 136, an elongated oval polyethylene basin recess, a bump 138 for holding surgical instruments, and two polyethylene specimen cup recesses 140.

The sterile barrier 150, initially accordion folded and removably attached to the drape panel 114, has a broad band of adhesive 160 applied to the rearmost (top of Brace 26) bottom edge of the rear panel 152, for securing the panel to the rear table top.

The barrier comprises two panels 152, 154 (FIG. 11), which are interconnected by the manufacturer along their overlapping edges by an adhesive zone 156 which allows the panels to be pulled apart later. "TEAR HERE" decals 158 are affixed to the upper surfaces of the panels, near the adhesive strip.

Figure 7:
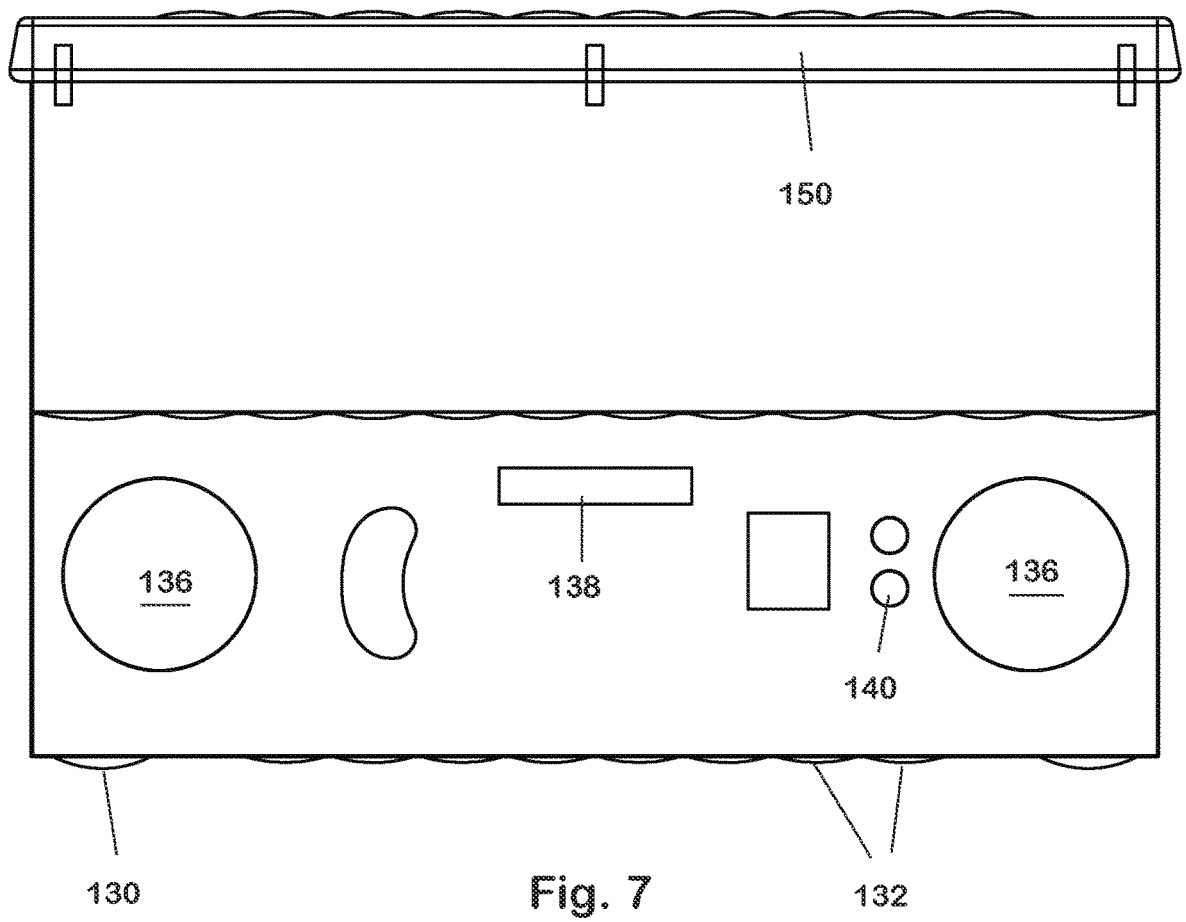
FIG. 7 is a top plan view thereof.

The sterile barrier 150, accordion folded as shown in FIGS. 6 and 7, is preattached to the drape by the manufacturer. A small adhesive tape strip 162 is secured to either forward corner of the front panel 154, its free end extending laterally outward. The tape strips 162 function as grip tabs which enable one to deploy the sterile barrier over a draped and stocked table.

The barrier can be removed to expose the sterile table and instruments on the table by peeling the two panels 152, 154 apart, after gripping the panels at the "TEAR HERE" decals 158.

While this invention has been described in terms of illustrated embodiments, it will be apparent to those of skill in the art that variations and modification may be made without departing from the concept, spirit and scope of the invention. It is therefore intended that the invention be defined by the appended claims.

We claim:

1. A tiered surgical table comprising:
   a chassis,
   a pair of front and rear table tops,
   each of said front and rear table tops being non-adjustably supported by the chassis,
   said front and rear table tops being situated at different heights so that the rear table top is higher and the front table top is lower,
   said front and rear table tops further being non-parallel to one another,
   the front and rear table tops each having front and rear edges,
   the front edge of the rear table top lying substantially vertically above the rear edge of the front table top, and
   the front table top having at least one aperture formed therein and the at least one aperture formed therein is configured to receive a basin.

2. A fitted drape for a tiered surgical table as recited in claim 1, said fitted drape comprising:
   a fitted drape having upper and lower top panels,
   a vertical step panel located between and interconnecting the upper top panel to the lower top panel,
   a front panel connected to the lower top panel, two side panels connected to both the upper and lower top panels, and a rear panel connected to the upper top panel, and the front panel, the rear panel and the two side panels each hang a distance below levels of the upper and lower top panels after the fitted drape is installed on the tiered surgical table,
   the lower top panel of the fitted drape having at least one polyethylene basin recess for mating with and extending into the at least one aperture formed in the front table top, and
   a sterile barrier being secured to the fitted drape in a folded position which permits access to the upper and lower top panels, but, after the sterile barrier is deployed over the upper and the lower top panels, the sterile barrier forms a barrier which restrict access to instruments supported by the upper and the lower top panels of the fitted drape.

3. The fitted drape of claim 2, further comprising a first array of pockets attached to said front panel, and a second array of pockets attached to said step panel.

4. A fitted drape for a tiered surgical table having features for holding surgical instruments and receptacles, said features including plural shaped apertures formed in at least one surface of the tiered surgical table, said drape comprising
   upper and lower top panels,
   a vertical step panel between the top panels
   a vertical step panel located between and interconnecting the upper top panel to the lower top panel,
   a front panel connected to the lower top panel, two side panels connected to both tops panels, and a rear panel connected to the upper top panel,
   wherein a front panel connected to the lower top panel and two side panels, the two side panels connected to both the upper and lower top panels, and a rear panel connected to the upper top panel and the two side panels,
   at least one of said upper and lower top panels having a flexible recess corresponding in shape and position to at least one of said shaped apertures in the tiered surgical table so that said flexible recess of the fitted drape can seat within and directly engage with said at least one of said irregularly shaped apertures in the tiered surgical table when the drape is fitted to the tiered surgical table.

5. The fitted drape for a tiered surgical table as recited in claim 4, wherein a sterile barrier being secured to the fitted drape in a folded position which permits access to the upper and lower top panels of the fitted drape, but, after the sterile barrier is deployed over the upper and lower top panels, the sterile barrier protects and restricts access to a draped and stocked tiered surgical table.

6. The fitted drape for a tiered surgical table as recited in claim 5, wherein after the sterile barrier is deployed over the upper and lower top panels to protect and restrict access to a draped and stocked tiered surgical table, an operator can remove the sterile barrier to expose the sterile instruments on the tiered surgical table.

7. A flexible fitted drape for a tiered surgical table, the fitted drape comprising:
an upper top panel and a lower top panel,
a vertical step panel being located between and interconnecting the upper top panel to the lower top panel,
a front panel connected to the lower top panel and two side panels, the two side panels connected to both the upper and lower tops panels and the step panel, and a rear panel connected to the upper top panel and the two side panels, and, following draping of a tiered surgical table, the front panel, the rear panel and the two side panels each hang a distance below levels of upper and lower top panels of the tiered surgical table, and
at least one of the upper and the lower top panels of the fitted drape having at least one flexible polyethylene basin recess formed therein for extending into and mating with at least one aperture formed in a mating table top of the tiered surgical table when the fitted drape is applied to the tiered surgical table.

8. The flexible fitted drape for the tiered surgical table as recited in claim 7, wherein the fitted drape has at least two spaced apart flexible polyethylene basin recesses formed therein for mating with and extending into at least two spaced apart apertures formed in a front table top of the tiered surgical table.

9. The flexible fitted drape for the tiered surgical table as recited in claim 7, wherein the fitted drape has at least two spaced apart flexible polyethylene basin recesses for mating with and extending into at least two spaced apart apertures formed in a front table top of the tiered surgical table, and
the fitted drape further has at least two spaced apart flexible polyethylene specimen cup recesses for mating with and extending into at least two spaced apart specimen cup apertures formed in the front table top of the tiered surgical table.

10. The flexible fitted drape for the tiered surgical table as recited in claim 7, wherein the front panel of the fitted drape has an array of pockets secured thereto, and
all of the array of pockets are secured, during manufacture, to material forming the fitted drape.

11. The flexible fitted drape for the tiered surgical table as recited in claim 7, wherein the front panel of the fitted drape has two refuse pockets, located adjacent either end of the front panel,
an array of other pockets located between the two refuse pockets, and
all of the array of pockets are secured to material forming the fitted drape during manufacture.

12. The flexible fitted drape for the tiered surgical table as recited in claim 7, wherein the rear panel of the fitted drape has an array of pockets for accommodating refuse.

13. The flexible fitted drape for the tiered surgical table as recited in claim 7, wherein the step panel of the fitted drape has an array of polyethylene storage pockets disposed along a width of the step panel.

14. The flexible fitted drape for the tiered surgical table as recited in claim 7, wherein the lower top panel of the fitted drape has a bump for supporting at least one surgical instrument.

15. The flexible fitted drape for the tiered surgical table as recited in claim 7, wherein the lower top panel of the fitted drape has two flexible polyethylene seven-quart basin recesses for mating with a respective basin hole of a front table top of the surgical table, an elongated oval polyethylene basin recess for mating with a respective oval shaped hole of the front table top, and two polyethylene specimen cup recesses for mating with respective specimen cups of the front table top.

16. The flexible fitted drape for the tiered surgical table as recited in claim 7, wherein a sterile barrier is secured to the fitted drape in a folded position which permits access to the upper and lower top panels of the fitted drape to facilitate stocking of the tiered surgical table but, after the sterile barrier is deployed over the upper and lower top panels of the draped and stocked tiered surgical table, the sterile barrier protects and restricts access to the draped and stocked tiered surgical table.

17. The flexible fitted drape for a tiered surgical table as recited in claim 16, wherein following deployment of the sterile barrier over the upper and lower top panels, access to sterile instruments, supported on the stocked tiered surgical table, can be provided by removing the sterile barrier to expose the surgical instruments.

18. The flexible fitted drape for the tiered surgical table as recited in claim 7, wherein an undersurface of the lower top panel directly engages with a top surface of a front table top of the tiered surgical table while an undersurface of the upper top panel directly engages with a top surface of a rear table top of the tiered surgical table, and
the at least one flexible polyethylene basin recess passes through the at least one aperture of the tiered surgical table when the fitted drape is applied to the tiered surgical table.

19. The flexible fitted drape for the tiered surgical table as recited in claim 7, wherein an undersurface of the lower top panel directly engages with a top surface of a front table top of the tiered surgical table while an undersurface of the upper top panel directly engages with a top surface of a rear table top of the tiered surgical table,
the at least one flexible polyethylene basin recess passes through the at least one aperture of the tiered surgical table when the fitted drape is applied to the tiered surgical table and directly engages with a basin supported by the tiered surgical table.

* * * * *